United States Patent
Hwang

(10) Patent No.: US 8,804,800 B2
(45) Date of Patent: Aug. 12, 2014

(54) FREQUENCY RESPONSE MEASUREMENT SYSTEM AND METHOD

(75) Inventor: Jung Hwan Hwang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 433 days.

(21) Appl. No.: 13/269,467

(22) Filed: Oct. 7, 2011

(65) Prior Publication Data

US 2012/0087651 A1 Apr. 12, 2012

(30) Foreign Application Priority Data

Oct. 8, 2010 (KR) .......................... 10-2010-0098263
Sep. 27, 2011 (KR) .......................... 10-2011-0097512

(51) Int. Cl.
*H04B 3/46* (2006.01)

(52) U.S. Cl.
USPC ........... 375/224; 375/219; 375/222; 375/259; 375/295; 375/354

(58) Field of Classification Search
CPC ....... H04B 7/24; H04B 3/468; H04J 13/0048; G01S 13/0209; G01S 13/106; G01S 13/887; G01S 7/414; G01V 3/30; H01P 1/2056; H01P 3/06; H04H 20/62; H04L 12/2697; H04L 43/50; H04R 5/04; H04N 2201/0471; H04N 2201/04755; H04N 2201/02439; H04N 2201/04732; H04N 2201/04744; H04N 2201/04794; H04N 5/211; H04N 5/4401; H04N 1/053; H04N 1/17
USPC ......... 375/213, 219, 222, 223, 224, 226, 259, 375/286, 293, 295, 316, 340, 354, 355
See application file for complete search history.

(56) References Cited

U.S. PATENT DOCUMENTS

| | | | | |
|---|---|---|---|---|
| 6,313,885 B1 * | 11/2001 | Patel et al. | ..................... | 348/725 |
| 6,483,253 B1 * | 11/2002 | Okamoto et al. | ............. | 315/219 |
| 7,076,177 B1 * | 7/2006 | Yang et al. | ..................... | 398/208 |
| 7,372,280 B2 * | 5/2008 | Steennis et al. | ............... | 324/536 |
| 7,933,266 B2 * | 4/2011 | Zadikian et al. | ............... | 370/389 |
| 7,957,653 B2 * | 6/2011 | Kawanishi et al. | ........... | 398/188 |
| 2006/0136015 A1 * | 6/2006 | Park et al. | ......................... | 607/60 |
| 2006/0153109 A1 * | 7/2006 | Fukumoto et al. | ............ | 370/310 |
| 2006/0164099 A1 * | 7/2006 | Steennis et al. | ............... | 324/536 |
| 2008/0287061 A1 * | 11/2008 | Kim et al. | ..................... | 455/41.1 |
| 2010/0098433 A1 * | 4/2010 | Boyd et al. | ..................... | 398/155 |
| 2010/0246643 A1 * | 9/2010 | Lim et al. | ...................... | 375/147 |
| 2011/0051780 A1 * | 3/2011 | Kawasaki | ...................... | 375/135 |
| 2011/0170636 A1 * | 7/2011 | Matsuya et al. | ............... | 375/319 |
| 2012/0038461 A1 * | 2/2012 | Forster | ......................... | 340/10.1 |
| 2012/0128036 A1 * | 5/2012 | Kang et al. | ..................... | 375/144 |
| 2014/0071801 A1 * | 3/2014 | Ho et al. | ......................... | 370/209 |

FOREIGN PATENT DOCUMENTS

| KR | 1020060012323 A | 2/2006 |
|---|---|---|
| KR | 1020090113525 A | 11/2009 |

* cited by examiner

*Primary Examiner* — Hirdepal Singh

(57) ABSTRACT

A frequency response signal transmitting device for frequency response measurement includes: a first oscillator unit configured to generate a clock signal; a clock and data recovery (CDR) unit configured to remove a jitter component of the clock signal; a pulse signal generation unit configured to receive an output signal of the CDR unit and generate a pulse signal repeated at a predetermined period; and an optical signal transmission unit configured to receive the output signal of the CDR unit and apply the received signal to an optical cable.

12 Claims, 4 Drawing Sheets

US 8,804,800 B2

FREQUENCY RESPONSE MEASUREMENT SYSTEM AND METHOD

CROSS-REFERENCES TO RELATED APPLICATIONS

The present application claims priority under 35 U.S.C 119(a) to Korean Application No. 10-2010-0098263, filed on Oct. 8, 2010 and Korean Application No. 10-2011-0097512, filed on Sep. 27, 2011 in the Korean intellectual property Office, which is incorporated herein by reference in its entirety set forth in full.

BACKGROUND

Exemplary embodiments of the present invention relate to a frequency response measurement system and method, and more particularly, to a frequency response measurement system and method which is capable of measuring a frequency response of a dielectric medium including a signal transmitter/receiver and an interface.

In a wireless communication apparatus for wireless communication among a plurality of information terminal devices, a variety of dielectric media including users and various structures may be positioned between the wireless communication apparatuses.

In order to estimate the performance of the wireless communication apparatus, measuring characteristics of the dielectric media is required. Based on the estimated performance, it is possible to design and manufacture a transmitter/receiver which is suitable for the characteristics of the dielectric media. A frequency response indicating an amplitude and phase change for each frequency signal in a specific frequency band may be used for evaluating the characteristics of the dielectric media.

A ground part of a wireless communication apparatus for wireless communication maintains a state in which it is electrically isolated at all times. Therefore, when a frequency response of dielectric media including a signal transmitter/receiver is measured, the isolation state of the ground part should be maintained to more accurately estimate the performance of the signal transmitter/receiver.

FIG. 1 is a diagram illustrating a signal transmission process between two wireless communication apparatuses 101 and 201 according to the related art.

Referring to FIG. 1, the respective wireless communication apparatuses 101 and 201 include signal transmitters/receivers 102 and 202 and interfaces 103 and 203, respectively. The signal transmitters/receivers 102 and 202 are configured to transmit/receive a signal. The interfaces 103 and 203 are configured to transfer a signal transmitted from the signal transmitter/receiver to a medium for wireless communication or transfer a signal transmitted through the medium to the signal transmitter/receiver.

The interfaces 103 and 203 may differ depending on use conditions. For example, when the interfaces 103 and 203 are not contacted with a medium for wireless communication, an antenna or signal coupler may be used as the interfaces 103 and 203, and when the interfaces 103 and 203 are contacted with the medium, an electrode or the like may be used as the interfaces 103 and 203. Depending on use conditions during signal transmission, a dielectric medium 100 such as a human body or surrounding object may be positioned between the wireless communication apparatuses 101 and 201.

Meanwhile, the respective wireless communication apparatuses 101 and 201 use ground parts 104 and 204 which are electrically isolated from each other, and the isolation state of the ground parts 104 and 204 should be maintained when the frequency response of the dielectric medium 100 including the signal transmitters/receivers 102 and 202 and the interfaces 103 and 203 is measured.

According to the related art, however, a method for effectively measuring the frequency response of the dielectric medium 100 including the signal transmitter/receivers 102 and 202 and the interfaces 103 and 203 in a state in which the ground parts 104 and 204 of the wireless communication apparatus are isolated has not yet been proposed.

SUMMARY

An embodiment of the present invention relates to a frequency response measurement system and method which is capable of measuring a frequency response of a dielectric medium including a signal transmitter/receiver and an interface, in a state in which ground parts of wireless communication apparatuses are electrically isolated from each other.

In one embodiment, a frequency response signal transmitting device for frequency response measurement includes: a first oscillator unit configured to generate a clock signal; a clock and data recovery (CDR) unit configured to remove a jitter component of the clock signal; a pulse signal generation unit configured to receive an output signal of the CDR unit and generate a pulse signal repeated at a predetermined period; and an optical signal transmission unit configured to receive the output signal of the CDR unit and apply the received signal to an optical cable.

The frequency response signal transmitting device may further include: a frequency mixer configured to convert a frequency band of the pulse signal; a second oscillator unit configured to decide the frequency band converted by the frequency mixer; and a filter unit configured to remove harmonic components generated by the frequency mixer.

In another embodiment, a frequency response measurement system includes: a frequency response signal transmitting device configured to transmit a generated pulse signal through a dielectric medium and transmit a synchronization signal synchronized with the pulse signal through an optical cable; a frequency response signal receiving device configured to receive the pulse signal transmitted through the dielectric medium and receive the synchronization signal through the optical cable; and a frequency response measuring device configured to measure the transmitted pulse signal and the received pulse signal based on the synchronization signal.

The frequency response signal transmitting device may convert the synchronization signal into an optical signal, and then apply the optical signal to the optical cable.

The frequency response signal receiving device may convert the synchronization signal into an electrical signal, and then apply the electrical signal to the frequency response measuring device.

The frequency response signal receiving device may include: an optical signal reception unit configured to convert the synchronization signal transmitted through the optical cable into an electrical signal; a filter unit configured to remove an interference signal applied from outside from the pulse signal; and an amplifier configured to amplify the amplitude of the pulse signal which is reduced by a loss component of the dielectric medium.

The frequency response measuring device may measure the transmitted pulse signal and the received pulse signal at different time points.

In another embodiment, a signal transmission method performed by the frequency response signal transmitting device includes: generating a pulse signal and a synchronization signal synchronized with the pulse signal; and applying the pulse signal and the synchronization signal to a dielectric medium and to an optical cable, respectively, to transmit the signals.

The signal transmission method may further include inputting the pulse signal to a frequency mixer to shift a frequency band, after the generating of the pulse signal.

In another embodiment, a frequency response measurement method performed by a frequency response measurement system includes: receiving a pulse signal transmitted through a dielectric medium and a synchronization signal transmitted through an optical cable; measuring the transmitted pulse signal based on the synchronization signal; measuring the received pulse signal based on the synchronization signal; and subtracting the transmitted pulse signal and the received pulse signal from a frequency band, and deriving a frequency response.

The frequency response measurement method may further include, after the receiving of the pulse signal: removing an interference signal applied from outside from the pulse signal; and amplifying the amplitude of the pulse signal which is reduced by a loss component of the dielectric medium.

In the measuring of the received pulse signal, the received pulse signal is measured at a different time point from the transmitted pulse signal.

BRIEF DESCRIPTION OF THE DRAWINGS

The above and other aspects, features and other advantages will be more clearly understood from the following detailed description taken in conjunction with the accompanying drawings, in which.

DESCRIPTION OF SPECIFIC EMBODIMENTS

Hereinafter, embodiments of the present invention will be described with reference to accompanying drawings. The present invention may, however, be embodied in different forms and should not be construed as limited to the embodiments set forth herein, but it should be understood that the idea of the present invention should be construed to extend to any alterations, equivalents and substitutes besides the accompanying drawings.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Although terms like a first and a second are used to describe various elements, the elements are not limited to the terms. The terms are used only to discriminate one element from another element.

The terminology used herein is for the purpose of describing particular embodiments only and is not intended to be limiting of the invention. As used herein, the singular forms are intended to include the plural forms as well, unless the context clearly indicates otherwise. It will be further understood that the terms "comprise", "comprising", "have" and/or "having", when used herein, specify the presence of stated features, integers, steps, operations, elements, and/or components, but do not preclude the presence or addition of one or more other features, integers, steps, operations, elements, components, and/or groups thereof.

Furthermore, terms such as " . . . part", " . . . unit", and " . . . module" mean a unit which processes one or more functions or operations, and may be implemented by hardware, software, or a combination of hardware and software.

When it is determined that a specific description for the related known technology unnecessarily obscures the purpose of the present invention, the detailed descriptions thereof will be omitted.

Figure 1:
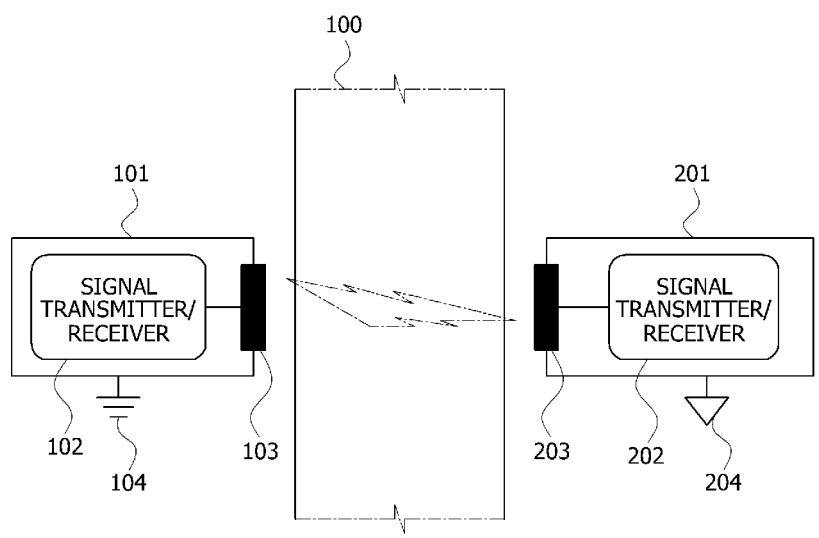
FIG. 1 is a diagram illustrating a signal transmission process between two wireless communication apparatuses according to the related art.
Figure 2:
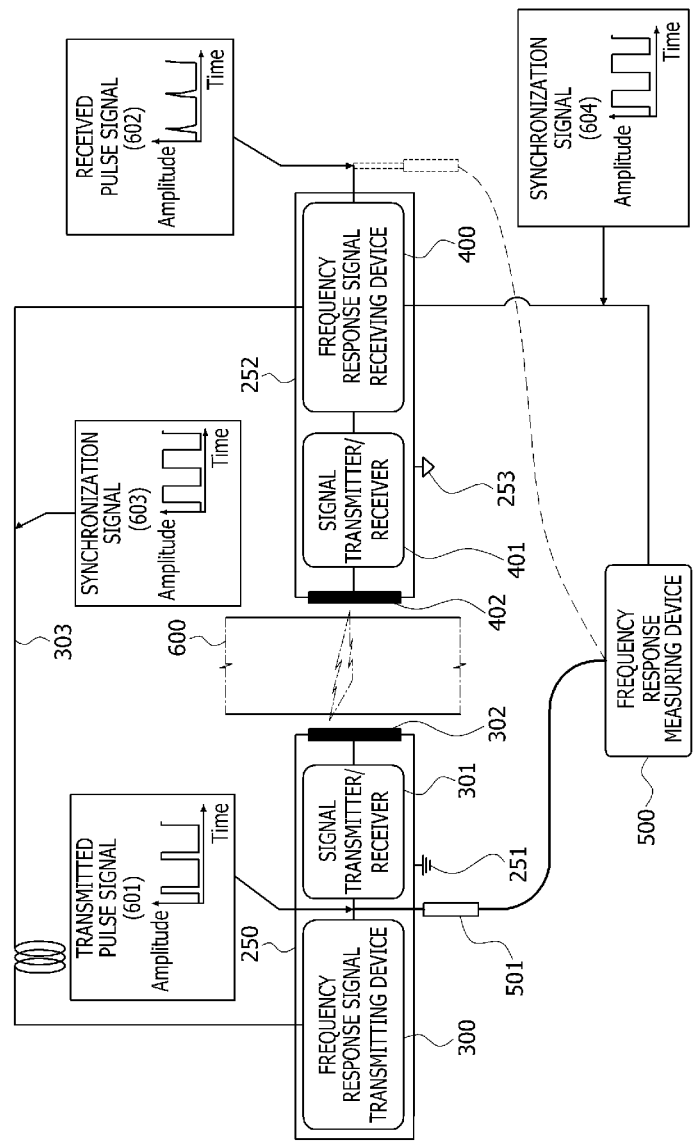
FIG. 2 is a configuration diagram of a frequency response measurement system in accordance with an embodiment of the present invention.

FIG. 2 is a configuration diagram of a frequency response measurement system in accordance with an embodiment of the present invention. The system in accordance with the embodiment of the present invention may use an optical signal transmission/reception method to transmit a synchronization signal.

Referring to FIG. 2, the frequency response measurement system in accordance with the embodiment of the present invention may include a frequency response signal transmitting device 300, a frequency response signal receiving device 400, and a frequency response measuring device 500.

The frequency response measurement system in accordance with the embodiment of the present invention is characterized in that it measures a frequency response of a dielectric medium including a transmitter/receiver and an interface, when the dielectric medium is positioned between wireless communication apparatuses for wireless communication. That is, when a ground part is not commonly formed between the wireless communication apparatuses, the frequency response measurement system may measure the frequency response of the dielectric medium including the transmitter/receiver and the interface while maintaining a condition in which the ground part is electrically isolated.

The operation of the frequency response measurement system in accordance with the embodiment of the present invention will be described as follows. The frequency response signal transmitting device 300 is configured to output a pulse signal 601 to a dielectric medium 600 through a signal transmitter/receiver 301 and an interface 302, and simultaneously transmit a synchronization signal 603 through an optical cable 303. The frequency response signal receiving device 400 is configured to receive a pulse signal 602 through the dielectric medium 600, an interface 402, and a signal transmitter/receiver 401, and simultaneously receive the synchronization signal 603 transmitted through the optical cable 303. The frequency response measuring device 500 measures the transmitted pulse signal 601 and the received pulse signal 602, based on the synchronization signal 603. Then, the frequency response measurement system derives the frequency response.

Specifically, the frequency response signal transmitting device 300 transmits the periodically-repeated pulse signal 601 to the dielectric medium 600 through the signal transmitter/receiver 301 and the interface 302. Furthermore, the frequency response signal transmitting device 300 converts an electrical signal synchronized with the pulse signal 601 into an optical signal and applies the optical signal to the optical cable 303 to transmit the synchronization signal 603.

When a frequency response which is to be acquired does not include the frequency response of a part or all of the signal transmitter/receiver 301, the part or all of the signal transmitter/receiver 301 may be removed before the frequency response is measured. Furthermore, the frequency response signal transmitting device 300 may be implemented on a substrate having the signal transmitter/receiver 301 implemented thereon and installed inside a wireless communication apparatus 250, or a part or all of the frequency response signal transmitting device 300 may be implemented in a separate module type and installed outside the wireless communication apparatus 250, when the internal space of the wireless communication apparatus 250 is small.

The frequency response signal receiving device 400 receives a signal transmitted through the dielectric medium 600, the interface 402, and the signal transmitter/receiver 401, and outputs the pulse signal 602. Simultaneously, the frequency response signal receiving device 400 receives the synchronization signal 603 transmitted through the optical cable 303 and converts the synchronization signal 603 into an electrical signal.

When a frequency response which is to be acquired does not include the frequency response of a part or all of the signal transmitter/receiver 401, the part or all of the signal transmitter/receiver 401 may be removed before the frequency response is measured. Furthermore, similarly as described above, the frequency response signal receiving device 400 may be implemented on a substrate having the signal transmitter/receiver 401 implemented thereon and installed inside a wireless communication apparatus 252, or a part or all of the frequency response signal receiving device 400 may be implemented in a separate module type and installed outside the wireless communication apparatus 252, when the internal space of the wireless communication apparatus 252 is small.

As the optical cable 303 is used to transmit the synchronization signal 603 instead of an electrical cable, the ground parts 251 and 253 of the wireless communication apparatuses 250 and 252 may maintain a state in which they are electrically isolated. Furthermore, as the synchronization signal 603 is transmitted in an optical signal form instead of an electrical signal form, the synchronization signal 603 becomes free from unwanted electromagnetic waves emitted from various electronic equipments existing around the measurement environment. Therefore, it is possible to measure the frequency response more accurately.

The frequency response measuring device 500 receives the synchronization signal 604 converted into an electrical signal by the frequency response signal receiving device 400, and measures the transmitted pulse signal 601 and the received pulse signal 602 by using a probe 501 included therein, based on the synchronization signal 604. The frequency response measuring device 500 first measures the transmitted pulse signal 601 in a state in which it is synchronized with the synchronization signal 604, and then measures the received pulse signal 602.

When a plurality of probes 501 are simultaneously connected to the wireless communication apparatuses 250 and 252 to measure the transmitted pulse signal 601 and the received pulse signal 602 at the same time, the ground parts 251 and 253 of the wireless communication apparatuses 250 and 252 are connected to each other through the probes 501. Therefore, the electrical isolation state between the ground parts 251 and 253 may not be maintained. Accordingly, in order to maintain the electrical isolation state between the ground parts 251 and 253, the transmitted pulse signal 601 and the received pulse signal 602 are not simultaneously measured, but are alternately measured at different time points by the probe 501. As the frequency response measuring device 500, a commonly-used spectrum analyzer or oscilloscope may be used.

Figure 3:
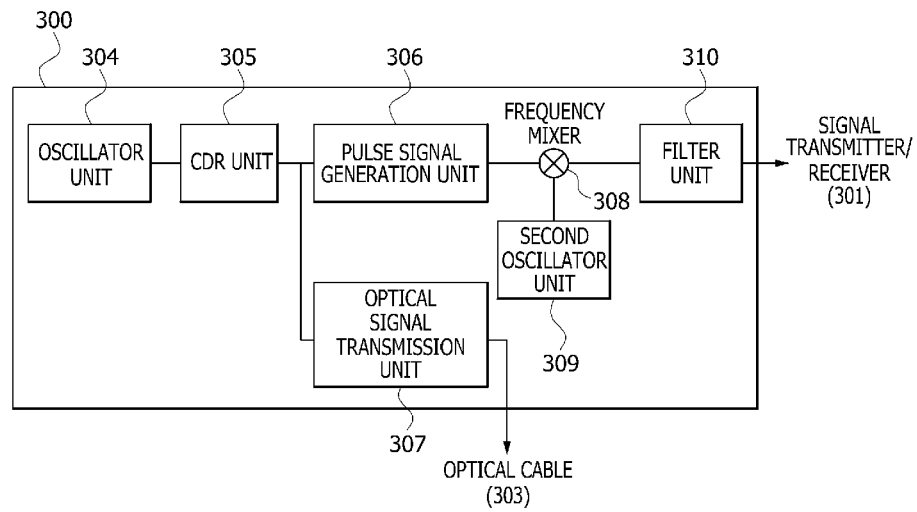
FIG. 3 is a diagram illustrating the detailed configuration of a frequency response signal transmitting device of FIG. 2.

FIG. 3 is a diagram illustrating the detailed configuration of the frequency response signal transmitting device 300 of FIG. 2.

Referring to FIG. 3, the frequency response signal transmitting device 300 includes an oscillator unit 304, a clock and data recovery (CDR) unit 305, a pulse signal generation unit 306, and an optical signal transmission unit 307. Furthermore, a frequency mixer 308, a second oscillator unit 309, and a filter unit 310 may be additionally used.

Specifically, the first oscillator unit 304 is configured to generate a clock signal having a predetermined frequency, and the CDR unit 305 is configured to receive the generated clock signal and remove a jitter component of the clock signal. Through the removal process, it is possible to reduce an error which occurs in the frequency response due to the jitter component of the clock signal.

The pulse signal generation unit 306 is configured to receive the clock signal from which the jitter component was removed and generate successive pulse signals having a period corresponding to the frequency of the clock signal. The pulse signal has a very narrow time slot. The pulse signal generation unit 306 causes the pulse signal to have a signal component in a wide frequency band, which makes it possible to acquire a frequency response in a wide band through one measurement.

When a frequency response needs to be measured on the basis of a specific frequency, the frequency mixer 308 and the second oscillator unit 309 may be separately installed at an output of the pulse signal generation unit 306, in order to shift the frequency band of the pulse signal into a specific frequency band. That is, the frequency of the second oscillator unit 309 may be controlled to control the frequency band of the pulse signal through the frequency mixer 308. Harmonic components generated by the frequency mixer 308 may be removed by the filter unit 310. Here, the oscillator unit 304 may be referred to as a first oscillator unit, in order to discriminate the oscillator unit from the second oscillator unit 309.

The optical signal transmission unit 307 is configured to receive the clock signal from which the jitter component was removed, convert the received clock signal into an electrical signal, and apply the electrical signal to the optical cable 303.

That is, the clock signal generated from the oscillator unit 304 is inputted to the pulse signal generation unit 306 and the optical signal transmission unit 307, after the jitter component of the clock signal is removed. The pulse signal outputted from the pulse signal generation unit 306 is transmitted to the dielectric medium 600 through the signal transmitter/receiver 301 and the interface 302, and the optical signal transmission unit 307 converts the same clock signal into an optical signal, and then transmits the optical signal through the optical cable 303. The signal outputted from the pulse signal generation unit 306 may be converted into a signal in a specific frequency band through the frequency mixer 308, the second oscillator unit 309, and the filter unit 310, if necessary.

Therefore, in the frequency response measurement system in accordance with the embodiment of the present invention, the pulse signal outputted from the frequency response signal transmitting device 300 is passed through the signal transmitter/receiver 301 and the interface 302 and then transmitted through the dielectric medium 600. Simultaneously, a synchronization signal synchronized with the pulse signal is converted into an optical signal and transmitted through the optical cable 303. The frequency response measuring device 500 measures the transmitted pulse signal 601 and the received pulse signal 602 based on the optical signal, thereby measuring the frequency response.

Here, the pulse signal transmitted through the dielectric medium 600 is inputted to the frequency response signal receiving device 400 through the interface 402 and the signal transmitter/receiver 401, and outputted after signal processing. The synchronization signal 603 transmitted through the optical cable 303 is converted into an electrical signal by the frequency response signal receiving device 400, inputted to the frequency response measuring device 500, and used as a synchronization signal.

Figure 4:
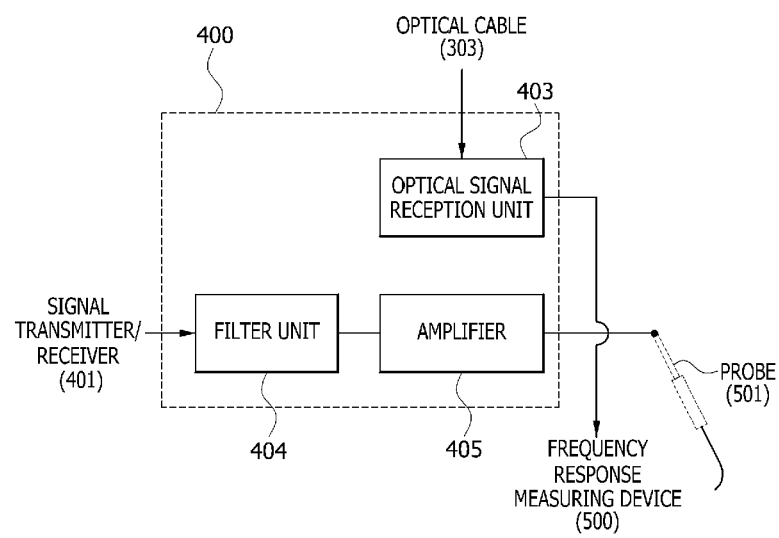
FIG. 4 is a diagram illustrating the detailed configuration of a frequency response signal receiving device of FIG. 2.

FIG. 4 is a diagram illustrating the detailed configuration of the frequency response signal receiving device 400 of FIG. 2.

Referring to FIG. 4, the frequency response signal receiving device 400 includes an optical signal reception unit 403, and a filter unit 404 and an amplifier 405 may be additionally used.

Specifically, the optical signal reception unit 403 is configured to receive the synchronization signal 603 transmitted from the frequency response signal transmitting device 300 through the optical cable 303, convert the received optical signal into an electrical signal, and transmit the electrical signal to the frequency response measuring device 500.

The amplitude of the pulse signal transmitted through the dielectric medium 600 is reduced by a loss component of the medium. When the amplitude is significantly reduced so as not to be measured by the frequency response measuring device 500, the amplifier 405 may be additionally used to increase the amplitude of the signal.

When the frequency response is acquired, the frequency response of the used amplifier 405 may be subtracted to acquire the frequency response by the dielectric medium 600, the interfaces 302 and 402, and the signal transmitters/receivers 301 and 401. When the pulse signal is transmitted through the dielectric medium 600, an interference signal may be generated by unwanted electromagnetic waves emitted from various electronic equipments existing around the measurement environment, and received by the frequency response signal reception device 400 together with the pulse signal. In this case, the filter unit 404 is used to remove the interference signal, which makes it possible to measure the frequency response more accurately.

Figure 5:
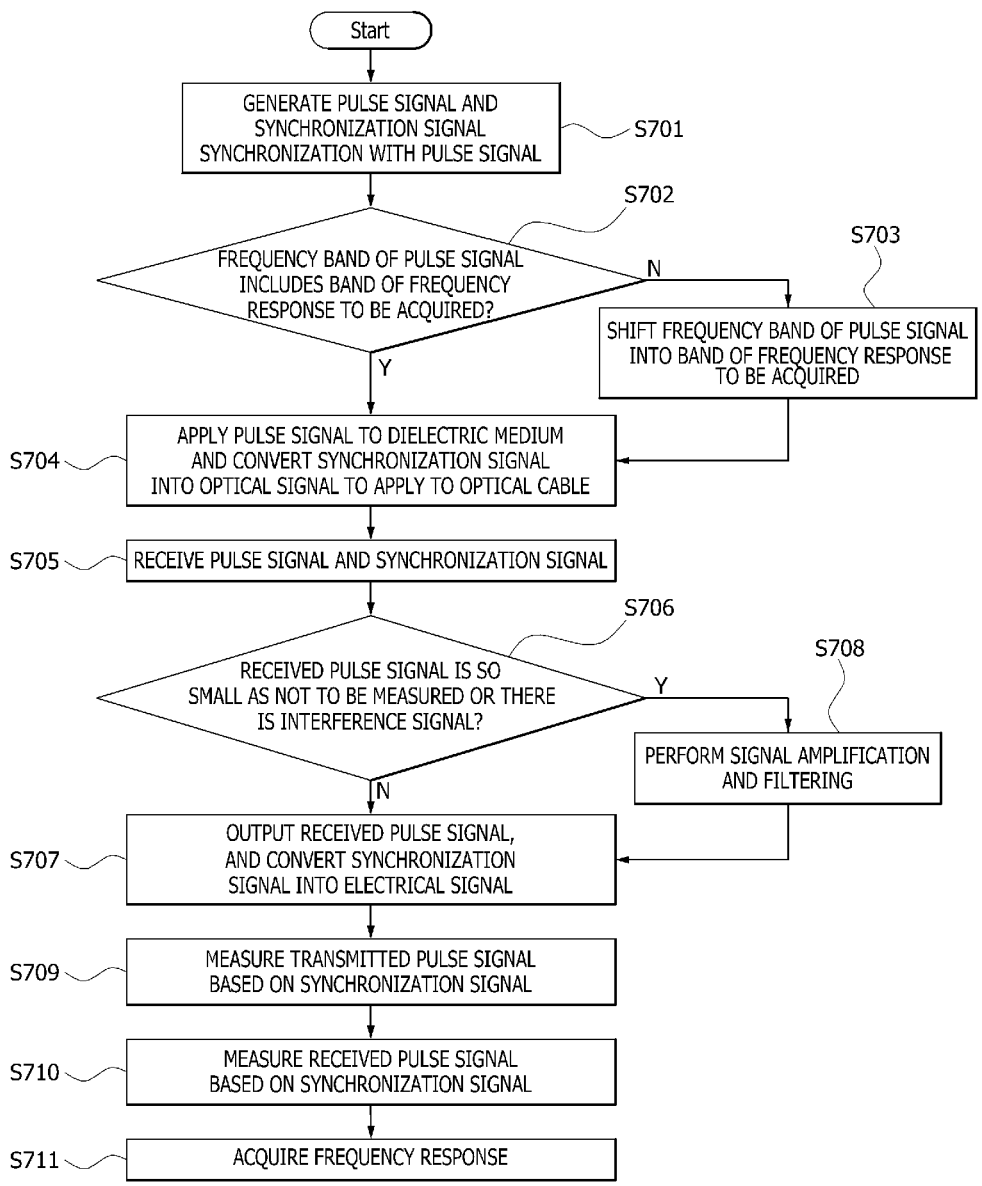
FIG. 5 is a flow chart showing a frequency response measurement method in accordance with the embodiment of the present invention.

FIG. 5 is a flow chart showing a frequency response measurement method in accordance with the embodiment of the present invention. The respective steps of the method may be performed by the wireless communication apparatuses 250 and 252 and the frequency response measuring device 500 as described above.

Referring to FIG. 5, the frequency response signal transmitting device 300 generates a pulse signal 601 and a synchronization signal 603 synchronized with the pulse signal 601 at step S701. Then, the frequency response signal transmitting device 300 applies the pulse signal 601 and the synchronization signal 603 to the dielectric medium 600 and the optical cable 303, respectively, to transmit the pulse signal 601 and the synchronization signal 603, at step S704.

Specifically, at the step S701, a clock signal is generated, a jitter component of the clock signal is removed, and the clock signal is inputted to the pulse signal generation unit 306 to generate the pulse signal. Simultaneously, the same clock signal is inputted to the optical signal transmission unit 307 to generate the synchronization signal in an optical signal form.

At step S702, whether the frequency band of the pulse signal 601 includes the band of a frequency response to be acquired or not is determined. When it is determined that the frequency band of the pulse signal 601 includes the band of the frequency response, the pulse signal 601 is transmitted to the dielectric medium 600 through the signal transmitter/receiver 301 and the interface 302 at the step S704. Otherwise, at step S703, the frequency mixer 308, the second oscillator unit 309, and the filter unit 310 which are separately installed are used to shift the frequency band of the pulse signal 601 into the band of the frequency response to be acquired. Then, the pulse signal is transmitted to the dielectric medium in the same manner, and simultaneously, the synchronization signal is converted into an optical signal to transmit through the optical cable, at the step S704.

At step S705, the pulse signal 602 transmitted through the dielectric medium and the synchronization signal 604 transmitted through the optical cable 303 are received. Then, the transmitted pulse signal 601 is measured on the basis of the synchronization signal 604 at step S709, and the received pulse signal 602 is measured at step S710.

Specifically, the pulse signal 602 transmitted through the dielectric medium 600 and the synchronization signal 604 transmitted through the optical cable 303 are received at the step S705. Then, whether or not the signal transmitted through the dielectric medium 600 is so small as not to be measured or whether or not there is an interference signal applied from outside is determined at step S706. When it is determined that the signal is so small as not to be measured or there is an interference signal, the received signal is outputted at step S707. Otherwise, a signal processing process of signal amplification and filtering is first performed at step 708.

Simultaneously, at the step S707, the synchronization signal having an optical signal form transmitted through the optical cable 303 is converted into an electrical signal. Then, the pulse signal 601 is measured on the basis of the synchronization signal 604 at step S709, and the received pulse signal 602 is measured at step S710.

At step S711, the measured pulse signal is subtracted from the frequency band to calculate a quantity of changes in amplitude and phase, thereby acquiring the frequency response. That is, the transmitted pulse signal 601 and the received pulse signal 602 may be subtracted from the frequency band to acquire the frequency response.

In accordance with the embodiments of the present invention, it is possible to measure a frequency response of a dielectric medium including a signal transmitter/receiver and an interface in a state in which ground parts of wireless communication apparatuses are electrically isolated from each other.

The embodiments of the present invention have been disclosed above for illustrative purposes. Those skilled in the art will appreciate that various modifications, additions and substitutions are possible, without departing from the scope and spirit of the invention as disclosed in the accompanying claims.

What is claimed is:

1. A frequency response signal transmitting device for frequency response measurement, comprising:
   a first oscillator unit configured to generate a clock signal;
   a clock and data recovery (CDR) unit configured to remove a jitter component of the clock signal;
   a pulse signal generation unit configured to receive an output signal of the CDR unit and generate a pulse signal repeated at a predetermined period; and
   an optical signal transmission unit configured to receive the output signal of the CDR unit and apply the received signal to an optical cable.

2. The frequency response signal transmitting device of claim 1, further comprising:

a frequency mixer configured to convert a frequency band of the pulse signal;

a second oscillator unit configured to decide the frequency band converted by the frequency mixer; and a filter unit configured to remove harmonic components generated by the frequency mixer.

3. A frequency response measurement system comprising:

a frequency response signal transmitting device configured to transmit a generated pulse signal through a dielectric medium and transmit a synchronization signal synchronized with the pulse signal through an optical cable;

a frequency response signal receiving device configured to receive the pulse signal transmitted through the dielectric medium and receive the synchronization signal through the optical cable; and a frequency response measuring device configured to measure the transmitted pulse signal and the received pulse signal based on the synchronization signal.

4. The frequency response measurement system of claim 3, wherein the frequency response signal transmitting device converts the synchronization signal into an optical signal, and then applies the optical signal to the optical cable.

5. The frequency response measurement system of claim 3, wherein the frequency response signal receiving device converts the synchronization signal into an electrical signal, and then applies the electrical signal to the frequency response measuring device.

6. The frequency response measurement system of claim 3, wherein the frequency response signal receiving device comprises:

an optical signal reception unit configured to convert the synchronization signal transmitted through the optical cable into an electrical signal;

a filter unit configured to remove an interference signal applied from outside from the pulse signal; and an amplifier configured to amplify the amplitude of the pulse signal which is reduced by a loss component of the dielectric medium.

7. The frequency response measurement system of claim 3, wherein the frequency response measuring device measures the transmitted pulse signal and the received pulse signal at different time points.

8. A signal transmission method performed by a frequency response signal transmitting device, comprising:

generating a pulse signal and a synchronization signal synchronized with the pulse signal; and applying the pulse signal and the synchronization signal to a dielectric medium and to an optical cable, respectively, to transmit the signals.

9. The signal transmission method of claim 8, further comprising inputting the pulse signal to a frequency mixer to shift a frequency band, after the step of generating the pulse signal.

10. A frequency response measurement method performed by a frequency response measurement system, comprising:

receiving a pulse signal transmitted through a dielectric medium and a synchronization signal transmitted through an optical cable;

measuring the transmitted pulse signal based on the synchronization signal;

measuring the received pulse signal based on the synchronization signal; and subtracting the transmitted pulse signal and the received pulse signal from a frequency band, and deriving a frequency response.

11. The frequency response measurement method of claim 10, further comprising, after the step of receiving the pulse signal:

removing an interference signal applied from outside from the pulse signal; and amplifying the amplitude of the pulse signal which is reduced by a loss component of the dielectric medium.

12. The frequency response measurement method of claim 10, wherein, in the step of measuring the received pulse signal, the received pulse signal is measured at a different time point from the transmitted pulse signal.

\* \* \* \* \*